United States Patent [19]
Dimmig et al.

[11] Patent Number: 5,482,638
[45] Date of Patent: Jan. 9, 1996

[54] METAL-FREE DITHIOPHOSPHORIC ACID DERIVATIVES

[75] Inventors: Thomas Dimmig, Jena; Günter Jäger, Freyburg; Thomas Petri, Jena, all of Germany

[73] Assignee: Rhein Chemie Rheinau GmbH, Mannheim, Germany

[21] Appl. No.: 165,423

[22] Filed: Dec. 6, 1993

[30] Foreign Application Priority Data

Dec. 16, 1992 [DE] Germany .......................... 42 42 501.8

[51] Int. Cl.[6] ...................... C10M 141/08; C10M 141/10
[52] U.S. Cl. .......................... 252/46.6; 208/18; 252/48.4; 252/56 R; 558/105; 558/161
[58] Field of Search .................... 252/46.6, 48.4; 558/194, 461, 105

[56] References Cited

U.S. PATENT DOCUMENTS

| | | | |
|---|---|---|---|
| 2,856,369 | 10/1958 | Smith et al. | 252/46.7 |
| 2,895,984 | 7/1959 | McCall et al. | 260/461 |
| 2,914,478 | 11/1959 | Nett | 252/46.6 |
| 3,023,209 | 2/1962 | Reese et al. | 252/46.7 |
| 3,112,335 | 11/1963 | Ronay et al. | 558/105 |
| 3,437,721 | 4/1969 | Baranauckas et al. | 558/105 |
| 3,929,653 | 12/1975 | Elliot et al. | 558/194 |
| 4,155,958 | 5/1979 | Fields | 260/926 |
| 4,416,797 | 11/1983 | Minagawa et al. | 252/400 A |
| 4,888,437 | 12/1989 | Zeidler et al. | 558/105 |
| 4,925,581 | 5/1990 | Erickson et al. | 252/49.8 |

FOREIGN PATENT DOCUMENTS 0818962 1/1956 United Kingdom .................. 558/105

OTHER PUBLICATIONS

Tetrahedron Lett [22], 1979 #288,666 Reaction of cyclohexene oxides with Phosphodiaeaters Toward Understanding The Reaction of Benzo(A)Pyrene Diol Epoxide With DNA.

*Primary Examiner*—Margaret Medley
*Attorney, Agent, or Firm*—Connolly & Hutz

[57] ABSTRACT

Addition products of monoepoxides or diepoxides of mono- or polyunsaturated monocyclic or bicyclic hydrocarbons and dithiophosphoric acids, a process for the production of the adducts from the corresponding dithiophosphoric acids and epoxides and the use of the addition products as lubricant additives in lubricants based on mineral oils or native oils.

7 Claims, No Drawings

METAL-FREE DITHIOPHOSPHORIC ACID DERIVATIVES

This invention relates to metal-free dithiophosphoric acid derivatives based on epoxidized, unsaturated cyclic hydrocarbons, to their production and to their use.

Metal dithiophosphates have long been successfully used as lubricant additives, above all for improving the anti-wear properties and resistance to ageing of mineral oils. Zinc dithiophosphates have proved to be particularly effective in this regard. However, they do not meet all the requirements which, in addition to those mentioned, an additive is expected to satisfy as a constituent of lubricants for modern machines. Thus, all metal dithiophosphates are so-called ash formers which can produce troublesome deposits on the lubricated friction elements. In addition, metal ions can delay the often desirable rapid biological degradation of the blended lubricants.

There has been no shortage of attempts to produce so-called ash-free (metal-free) dithiophosphates which would not have any of the disadvantages mentioned above. For example, efforts have been made to neutralize dithiophosphoric acids by addition onto unsaturated hydrocarbons. However, the reactions are incomplete, the reaction products are only partly soluble in the usual basic oils and lead to a deterioration in their ageing resistance. In addition, metal-free dithiophosphates, for example, have been developed by reaction of dithiophosphoric acids—produced from sulfurized alcohols and $P_4S_{10}$—with epoxidized oligomeric propylene and have been proposed as corrosion inhibitors by virtue of their specific properties.

The problem addressed by the present invention was to find derivatives of dithiophosphoric acids which would be metal-free and readily soluble in the usual basic oils, would improve the anti-wear properties and resistance to ageing of the basic oils and would be comparable with zinc dithiophosphates in their effectiveness based on these properties.

According to the invention, this problem has been solved by dithiophosphoric acid derivatives of epoxidized monocyclic or bicyclic hydrocarbons.

Accordingly, the present invention relates to addition products of monoepoxides or diepoxides of mono- or polyunsaturated monocyclic or bicyclic hydrocarbons and dithiophosphoric acids differing in the structure of their alkyl, aryl or mixed alkyl/aryl groups. Suitable epoxides are, for example, the monoepoxide or diepoxide of dicyclopentadiene. Suitable dithiophosphoric acids are, for example, O,O'-dialkyl, O,O'-diaryl or O,O'-alkyl/aryl dithiophosphoric acids of which the alkyl groups may be branched or unbranched and of which the aryl groups may be alkylated.

According to the invention, the problem, stated above has been solved by a process for the production of metal-free dithiophosphoric acid derivatives in which one of the reaction components, preferably the dithiophosphoric acid, is introduced into a stirred reactor and the other component, preferably the epoxide, is then added at such a rate that the exothermic chemical reaction thus initiated takes place at a reaction temperature of 30° to 100° C.

The present invention also relates to the production of the addition products of mono- or diepoxides of monounsaturated or polyunsaturated monocyclic or bicyclic hydrocarbons and dithiophosphoric acids. The two components mentioned may be smoothly and completely reacted in a molar ratio of 1:1, based on dithiophosphoric acid and epoxide groups, at temperatures in the range from 30° to 100° C. The reaction is exothermic and may readily be controlled by addition of preferably the epoxide in portions.

According to the invention, the solution to this problem is characterized in that the metal-free dithiophosphoric acid derivatives formed by reaction of epoxides with dithiophosphoric acids are dissolved in the basic oil of a lubricant—consisting of a mineral oil or a natural oil—and improve the anti-wear properties and the resistance to ageing of the basic oil.

The present invention also relates to the use of the described addition compounds to improve the properties of lubricants based on mineral oils or native oils. The addition compounds are readily soluble in the basic liquids and show anti-wear and anti-ageing activity in the usual tests.

The invention is illustrated by the following Example.

Example 1

The Example shows a metal-free dithiophosphoric acid derivative obtained by reaction of DCPD diepoxide with an O,O'-dialkyl dithiophosphoric acid in accordance with the following equation:

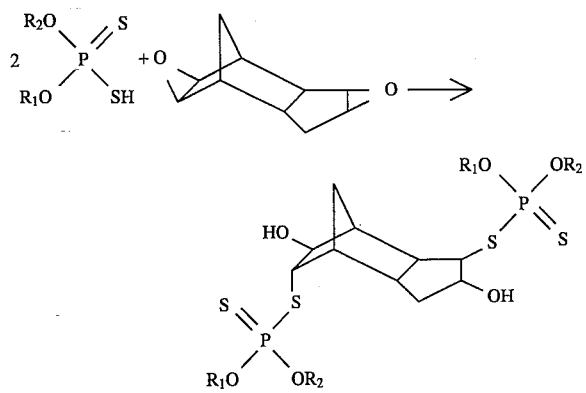

DTPS  dicyclopentadiene diepoxide $R_1$, $R_2$ = alkyl or aryl.

The process for the production of metal-free dithiophosphoric acid derivatives under laboratory conditions is described by way of example in the following:

0.2 ml 2-ethylhexyl dithiophosphoric acid is introduced into a 250 ml three-necked flask equipped with a reflux condenser, internal thermometer, stirrer and nitrogen inlet pipe and heated to 35° C. 0.1 mol dicyclopentadiene diepoxide is added in 4 equal portions so that the internal temperature does not exceed 60° C. After a total reaction time of 1 hour at 60° C., the reaction mixture is heated to 90–95° C. The reaction mixture is stirred at that temperature until the total reaction time is 4 hours. The reaction product is a light, clear highly viscous liquid. The compound has a sulfur content of 14.6% and a phosphorus content of 7.1%. The viscosity of the product at 40° C. is approx. 1,500 $mm^2/s$.

Performance testing of the product in the laboratory for its anti-wear properties and resistance to ageing produced the following results:

| Lubricant | Test methods | | |
| --- | --- | --- | --- |
| | VKA[1] | FZG[2] | Ageing test[3] |
| Colza oil/rapeseed oil | 0.70 | 10 | n.d. |
| Mineral oil | 1.0 | n.d. | 112 |

-continued

| Lubricant | Test methods | | |
|---|---|---|---|
| | VKA[1] | FZG[2] | Ageing test[3] |
| Product in colza oil | 0.56[4] | n.d. | n.d. |
| Product in mineral oil | 0.56[4] | 10[4] | 14.6[5] |

[1]Four-ball apparatus
Test period 1 h
Test force 300 N
Measured: wear mark diameter (mm)
[2]FZG test
Measured: load stage reached These results reflect the increase in protection against wear and resistance to ageing by using products according to the invention as additives.

The Example demonstrates the suitability of the metal-free dithiophosphoric acid derivatives according to the invention as additives in natural and mineral oils.

We claim:

1. Metal-free dithiophosphoric acid derivatives, obtained by reaction of dialkyl, diaryl or mixed alkyl/aryl dithiophosphoric acids with dicyclopentadiene diepoxide.

2. The metal-free dithiophosphoric acid derivatives of claim 1, wherein the dithiophosphoric acid is 2-ethylhexyl dithiophosphoric acid.

3. The metal-free dithiophosphosphoric acid derivatives of claim 1, wherein the dithiophosphoric acid is selected from the group consisting of 0,0'-dialkyl dithiophosphoric acid, 0,0'-diaryl dithiophosphoric acid or 0,0'-alkyl/aryl dithiophosphoric acid.

4. A method of improving the anti-wear properties and the resistance to ageing of a lubricant containing a basic oil using the metal-free dithiophosphoric acid derivatives of claim 1, wherein said metal-free dithiophosphoric acid derivatives are added to the basic oil of the lubricant.

5. The method of claim 4, wherein the basic oil of the lubricant is a mineral oil.

6. The method of claim 4, wherein the basic oil of the lubricant is a natural triglyceride.

7. The method of claim 4, wherein the basic oil of the lubricant is a natural oil.

* * * * *

UNITED STATES PATENT AND TRADEMARK OFFICE
CERTIFICATE OF CORRECTION

PATENT NO. : 5,482,638
DATED : January 9, 1996
INVENTOR(S) : Thomas Dimmig, et al.

It is certified that error appears in the above-indentified patent and that said Letters Patent is hereby corrected as shown below:

On the cover page, in item [56] References Cited, OTHER PUBLICATIONS subsection, "Phosphodiaeaters" should be --Phosphodiesters--.

At Column 4, line 2, "dithlophosphoric" should be --dithiophosphoric--. At Column 4, line 4, "dithiophosphphoric" should be --dithiophosphoric--.

Signed and Sealed this

Fifth Day of November, 1996

*Attest:*

BRUCE LEHMAN

*Attesting Officer*   *Commissioner of Patents and Trademarks*